(12) United States Patent
Geist (10) Patent No.: US 8,758,383 B2
(45) Date of Patent: Jun. 24, 2014

(54) DEPTH CONTROLLED JAMSHIDI NEEDLE

(75) Inventor: Wyatt Drake Geist, Davie, FL (US)

(73) Assignee: Safe Wire Holding, LLC, Davie, FL (US)

( * ) Notice: Subject to any disclaimer, the term of this patent is extended or adjusted under 35 U.S.C. 154(b) by 57 days.

(21) Appl. No.: 13/409,483

(22) Filed: Mar. 1, 2012

(65) Prior Publication Data

US 2012/0226301 A1      Sep. 6, 2012

Related U.S. Application Data

(60) Provisional application No. 61/448,030, filed on Mar. 1, 2011.

(51) Int. Cl.
*A61B 17/34* (2006.01)

(52) U.S. Cl.
USPC ........................................... 606/185; 606/172

(58) Field of Classification Search
USPC ................... 606/184, 185, 167–170, 172; 600/562–564, 566–567; 604/117, 264, 604/272, 274, 161–162, 164.01–164.12, 604/165.01, 165.02, 533–535
See application file for complete search history.

(56) References Cited

U.S. PATENT DOCUMENTS

| | | | | |
|---|---|---|---|---|
| 4,469,109 | A * | 9/1984 | Mehl | 600/566 |
| 5,368,046 | A * | 11/1994 | Scarfone et al. | 600/567 |
| 5,458,579 | A | 10/1995 | Chodorow et al. | |
| 6,033,411 | A | 3/2000 | Preissman | |
| 7,179,244 | B2 * | 2/2007 | Smith et al. | 604/110 |
| 7,399,294 | B2 * | 7/2008 | Mickley | 604/117 |
| 7,678,077 | B2 | 3/2010 | Harris et al. | |
| 8,221,358 | B2 * | 7/2012 | McKay | 604/187 |
| 2003/0163062 | A1 * | 8/2003 | Bauer | 600/567 |
| 2004/0077973 | A1 * | 4/2004 | Groenke et al. | 600/567 |
| 2010/0069843 | A1 * | 3/2010 | Allee et al. | 604/117 |

* cited by examiner

*Primary Examiner* — David Eastwood
(74) *Attorney, Agent, or Firm* — McHale & Slavin, P.A.

(57) ABSTRACT

A precision depth guided instrument, such as a Jamshidi needle, is provided for use in various surgeries related to the vertebrae. The instrument includes an outer cannula, an inner cannula and a stylet. After the cortical bone of a vertebra is penetrated by the outer cannula of the instrument, the depth of penetration of the inner cannula is adjusted by rotation of a stop mounted to the outer cannula. The inner cannula is then moved further into the vertebrae, and a stop mounted on the outer cannula controls the depth of penetration of the inner cannula. The correct depth of penetration is determined by radiography prior to the procedure.

15 Claims, 11 Drawing Sheets

DEPTH CONTROLLED JAMSHIDI NEEDLE

CROSS REFERENCE TO RELATED APPLICATION

This application claims priority under 35 USC 119(e) to the U.S. Application No. 61/448,030, filed Mar. 1, 2011, entitled, "Depth Controlled Jamshidi Needle", the contents of which are incorporated herein in their entirety.

FIELD OF THE INVENTION

The present invention relates to instruments employed for controlling accurate placement of devices, such as Jamshidi needles, used in spinal surgery. In particular, the present invention enables a surgeon to accurately control the depth into the vertebrae that devices used in spinal surgery will be placed.

BACKGROUND OF THE INVENTION

Medical procedures involving the vertebrae are normally complicated because of the preciseness and accuracy required to avoid both neural damage and injury to major blood vessels. Precision depth guided instruments are required to perform percutaneous spinal surgery. These surgeries sometimes require penetration of the hard cortical bone of the vertebra and traversal of the softer cancellous bone lying thereunder. A large force is normally required by the surgeon to penetrate the cortical bone. Once the cortical bone is penetrated, extreme care must then be taken to avoid rapidly penetrating through all of the cancellous bone. There is also the danger of rapidly passing through the cancellous bone and then through the cortical bone on the other side of the vertebra. This can result in injury or damage to the spinal cord and/or other organs or blood vessels located adjacent the spine. In some instances, the force required to penetrate the cortical bone is greater than a surgeon can apply by hand. In these instances a hammer or other similar instrument is required to force the instrument through the cortical bone. When a hammer or similar instrument is used, there is a greater danger of the instrument passing rapidly through the cancellous bone and out the other side of the vertebra.

DESCRIPTION OF THE PRIOR ART

U.S. Pat. No. 5,458,579 discloses an apparatus for inserting a trocar/cannula assembly through a wall of an anatomical cavity of an individual. The apparatus includes a housing for holding the trocar/cannula assembly, a device for driving the trocar/cannula assembly into the individual, a spine and a depth stop element mounted on the spine to control the depth which the trocar/cannula assembly is inserted into the individual.

U.S. Pat. No. 6,033,411 discloses a depth guided instrument for use in performing percutaneous implantation of hard tissue implant materials. A depth guided stylet includes a point adapted for piercing hard tissue and self-tapping threads for self tapping into hard tissue. The instrument also includes a cannula surrounding the stylet which employs a pawl and rack of gear teeth to assist passing the cannula through the hard tissue.

U.S. Pat. No. 7,678,077 discloses an instrument for injecting therapeutic and other agents into an individual at a target site. The instrument includes a catheter having a first elongate shaft and a second elongate shaft slidingly disposed within the first shaft. An indicator is secured to an end of the second elongate shaft and moves relative to a scale to indicate the position of the first and second shafts relative to their insertion into an individual.

None of the above noted prior art devices permit the operator of the device to adjust the depth of penetration of the Jamshidi needle or cannula based on information obtained from a patient prior to surgery. The depth of penetration can be adjusted depending on the point of entry into the body of the Jamshidi needle or cannula.

SUMMARY OF THE INVENTION

A precision depth guided instrument, such as a Jamshidi needle, is provided for use in various surgeries related to the vertebrae. The instrument includes an outer cannula, an inner cannula and a stylet. After the cortical bone of a vertebra is penetrated by the outer cannula of the instrument, the depth of penetration of the inner cannula is adjusted by rotation of a stop mounted to the outer cannula. The inner cannula is then moved further into the vertebrae, and a stop mounted on the outer cannula controls the depth of penetration of the inner cannula. The correct depth of penetration is determined by radiography prior to and during the procedure.

Accordingly, it is an objective of the instant invention to provide a device which can be inserted into a patient to an exact location.

It is a further objective of the instant invention to provide a device which can be inserted into a vertebra and then a portion of the device controllably moved to an exact location within the vertebra.

It is yet another objective of the instant invention to provide a device which can be inserted into a vertebra a measured distance, the measured distance having been predetermined by radiography.

It is a still further objective of the invention to provide a device which can be inserted into a vertebra an exact distance without any danger of exceeding the desired distance.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

FIGS. 1-11, which are now referenced, illustrate the present invention and the manner in which it is assembled. Like reference numerals refer to like components in the various figures. The needle depth controlled Jamshidi assembly 10 comprises a Jamshidi-type needle 12, and an outer cannula assembly 14. The Jamshidi-type needle 12 is slidably disposed within the outer cannula assembly 14. The Jamshidi-type needle 12 includes a cannula 16 which is secured to a handle 18. The handle 18 includes a collar or cylindrical portion 20. This cylindrical portion 20 is fixedly secured to the cannula 16. The handle 18 preferably has an ergonomic shape that can comfortably fit into a surgeon's or medical technician's hand. The handle includes an upper 15 curved portion which is shaped to conform to an individual's palm. The lower portion of the handle 18 is also curved. The curve of the lower portion of the handle is designed to be grasped by the fingers of an individual to assist in the control of the Jamshidi-type needle 12. The handle 18 is used to drive the cannula into, and sometimes through bones of a vertebra. Sometimes the Jamshidi-type needle 12 can be driven through the bone only by using pressure exerted by an individual's hand. Other times a hammer or other instrument must be employed to drive the needle 12 through a bone. There is a risk that, when a hammer or similar instrument is utilized, the Jamshidi-type needle 12 will pass too far into a vertebra. This can cause damage to nerves located nearby. Sometimes the needle passes completely through the vertebra and injures an adjacent blood vessel or internal organ. To prevent this, the present invention utilizes a second cannula 14 which is adjustably secured to the Jamshidi-type needle 12 to provide controlled linear traversal of the Jamshidi-type needle within the outer cannula assembly 14.

Figure 5:
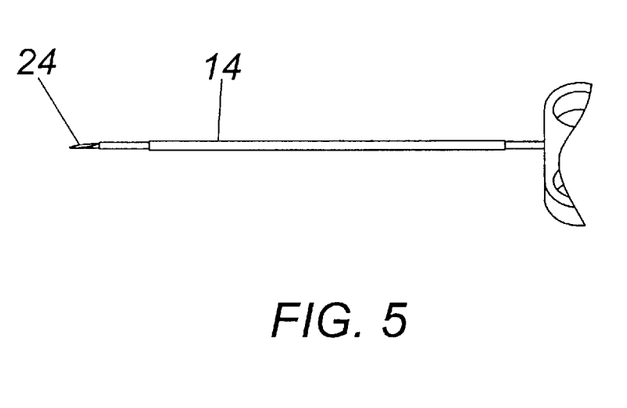
FIG. 5 is a view of the end portion of the present invention illustrating the relationship of the two cannulae and needle.

A needle 22 is slidably positioned within the cannula 16 of the Jamshidi-type needle 12. The preferred embodiment of the present invention illustrates the needle 22 as having a conical tip 24 (FIGS. 5). However, other tips and needles can also be employed. For example, a trocar needle 22 can be utilized. The tip 24 can be tapered, hollow, etc. The tip can be utilized to extract a tissue sample. It can also be utilized to anchor the needle 22 to a bone. An orthopedic bone screw or other device can then be passed down the needle 22 and secured to the correct location on a bone. While the preferred embodiment of the present invention discloses a relatively rigid needle 22, other needles which are flexible can also be employed.

Figure 1:
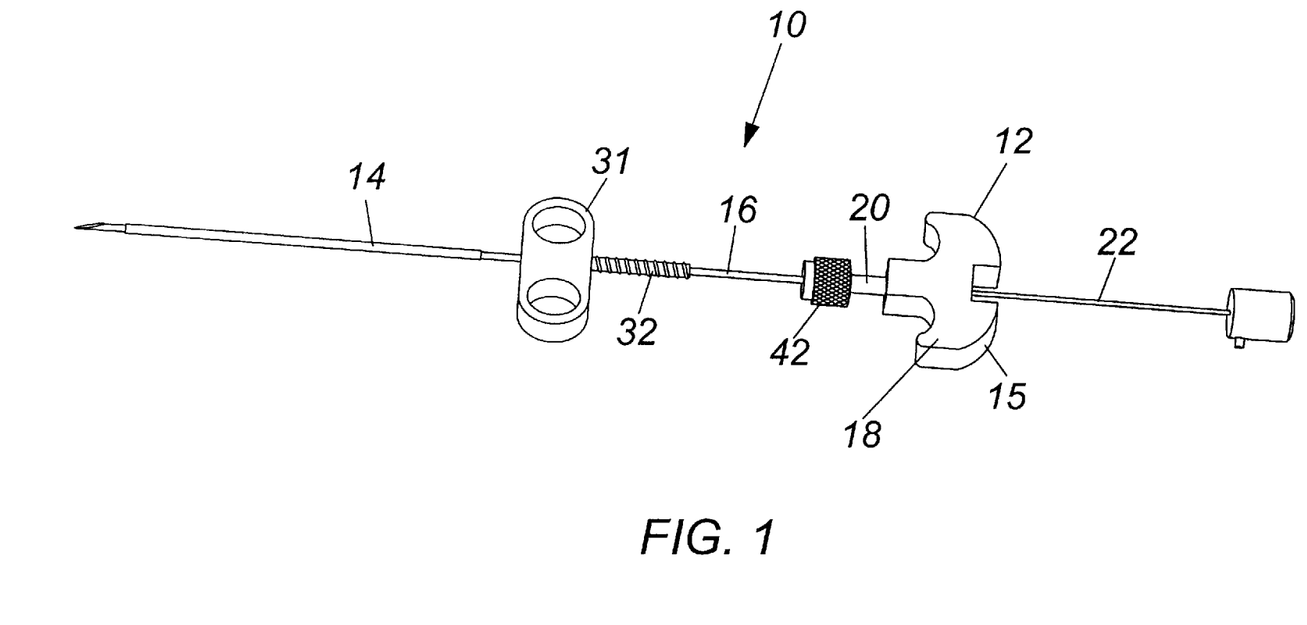
FIG. 1 is a perspective view of the invention with the components partially spaced from each other.
Figure 2:
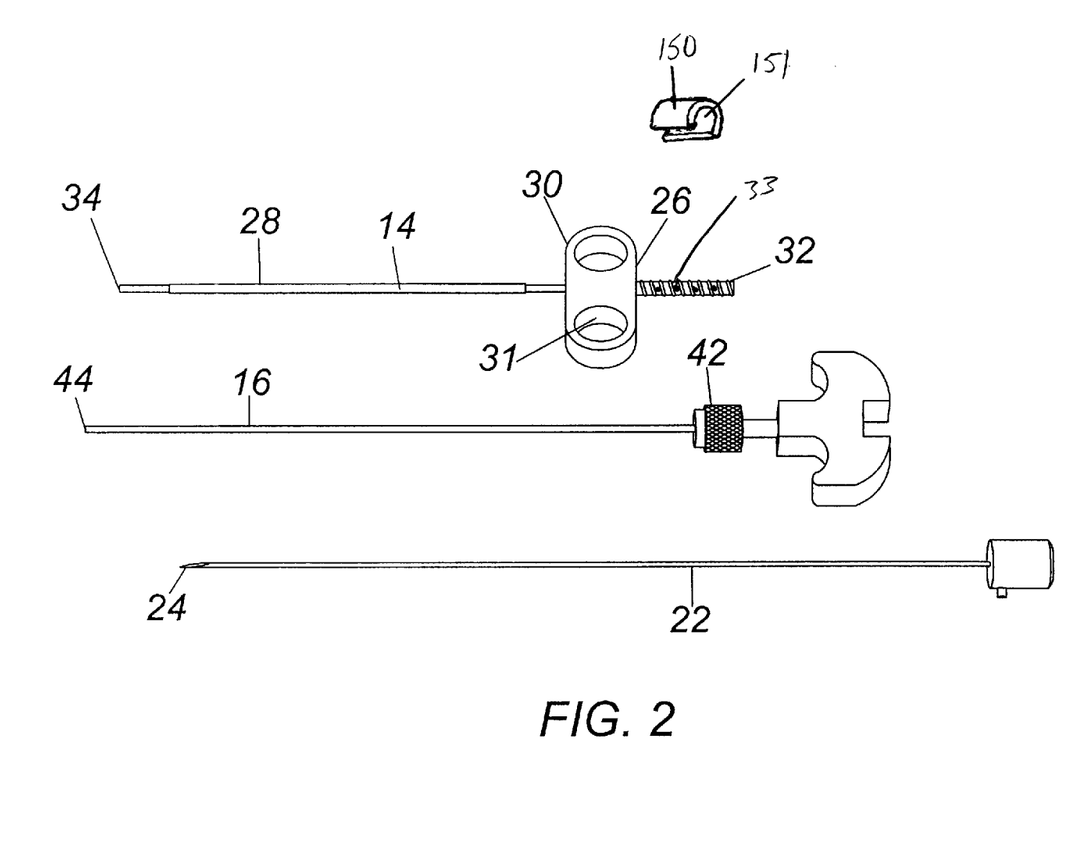
FIG. 2 is an exploded view of the present invention.

The outer cannula 14 comprises an upper portion 26 secured to a cannula 28 (FIG. 2). The upper portion 26 comprises a handle or grip 30 and a threaded sleeve 32. In the preferred embodiment of the outer cannula, the handle 30 and the threaded sleeve 32 are fixedly secured to each other. In other embodiments, these elements can be pivotably or removably secured to each other. The lower or second end 34 of the outer cannula 14 is constructed and arranged to penetrate and pass through bone. While the lower end 34 is normally a hollow tube with an end that tapers to a sharp edge, other edges can also be employed. For example, the edge can be serrated, saw toothed or sinusoidal. The smooth edge is preferably utilized when the needle assembly is driven straight into or through a bone. The serrations or waves are employed when additional effort is required to penetrate a bone. The handle or grip 30 is preferably provided with apertures 31 into which a surgeon's fingers can be inserted to control the device.

Figure 7:
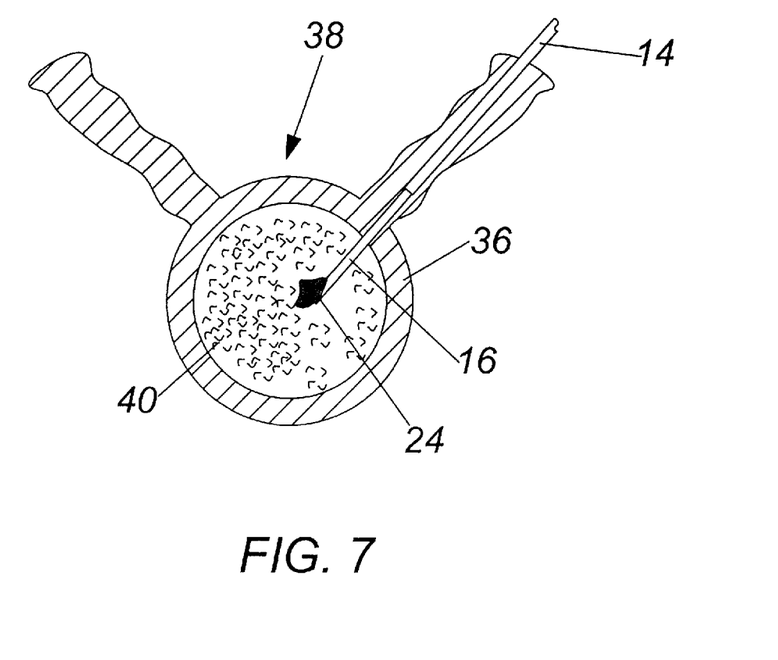
FIG. 7 is a cross sectional view of the present invention in a vertebra.

FIG. 7 illustrates an example of one of the uses of the present invention. The outer cannula 14, the cannula 16 and the tip 24 of the needle 22 are passed through a cortical bone 36 of a vertebra 38 and into the cancellous bone 40. A sample of the cancellous bone may now be taken. In another situation, the needle 22 may be passed into the cortical bone 36 opposite the point of insertion into the vertebra. In these different situations it is very difficult for a surgeon or medical technician to judge the depth of penetration of the depth controlled Jamshidi type needle 10 into the vertebra. The remedy for this problem lies in the present invention. First, a radiography image of the vertebra being operated upon is taken. Next, the depth into the vertebra that the surgeon wants the needle to penetrate is measured or estimated.

The Jamshidi-type needle 12 of the present invention includes a threaded nut 42 or similar device which is rotatably secured to the cannula 16 by a bearing. The threads on the nut 42 match the threads on the sleeve 32. After the surgeon inserts the needle into a patient and through the cortical bone 36 of a vertebra, the cannula 16 is inserted further into the vertebra by rotating the nut 42. Rotation of the nut 42 moves the cannula and needle 22 further into the vertebra. The distance that these elements are moved can be measured along the threaded sleeve. The distance the needle needs to travel into the vertebra, which has been determined by radiography, will be measured along sleeve 32. Preferably a mark or indicia 33 is then placed on sleeve 32.

The surgeon or medical technician can now rotate the nut 42 until it reaches the desired mark of indicia on sleeve 32. At this point, the cannula 16 and needle 22 are now exactly where they need to be positioned. The nut can be rotated by hand or with a wrench or similar device. The wrench may be utilized if a relatively hard bone is to be penetrated by the device.

In an alternate embodiment, the nut 42 is fixedly secured to the collar 20 and handle or grip 30. In this embodiment the handle 30 is rotated, which in turn rotates the collar 20 and nut 42. This moves the cannula 16 further into the vertebra until the desired position is reached. Rotation of handle 30 permits additional torque to be applied to the nut 42, and in certain instances does not required the use of a wrench or similar tool.

Figure 3:
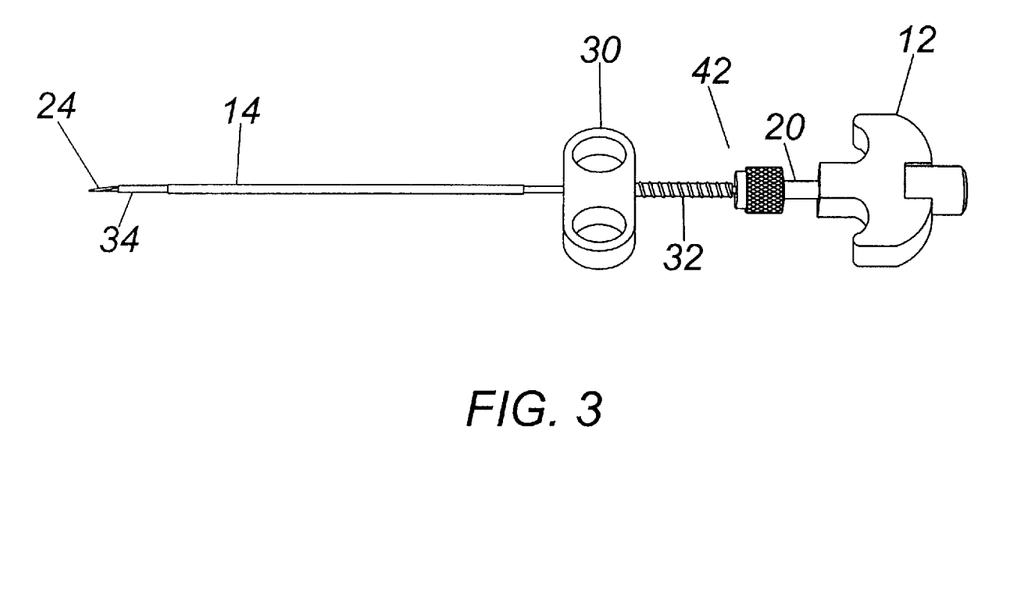
FIG. 3 is a view of the invention prior to insertion into a patient.
Figure 4:
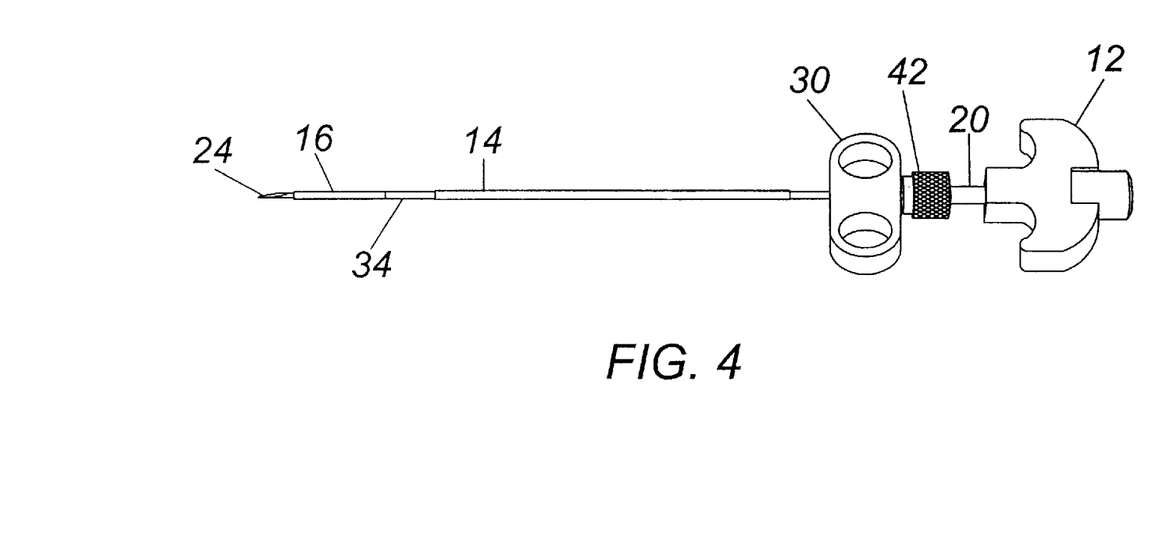
FIG. 4 is a view of the invention after an inner cannula has been moved further into a vertebra.

FIG. 3 illustrates the position of the elements of the invention prior to rotation of nut 42. The end of cannula 16 is adjacent the end 34 of the outer cannula. The tip 24 of the needle 22 protrudes slightly past this point. As illustrated in FIG. 4, after nut 42 is rotated, the inner cannula 16 and needle 22 move past the end 34 of cannula 14. The distance that the inner cannula 16 and needle move past the end 34 of cannula 14 has been previously determined by radiography. The end 44 (FIG. 2) of cannula 16 can be similar in construction to end 34 of cannula 14. While the end 44 is normally a hollow tube with an end that tapers to a sharp edge, other edges can also be employed. For example, the edge can be serrated, saw toothed or sinusoidal. The smooth edge is preferably utilized when the needle assembly is driven straight into or through a bone. The serrations or waves are employed when additional effort is required to penetrate a bone.

Figure 6:
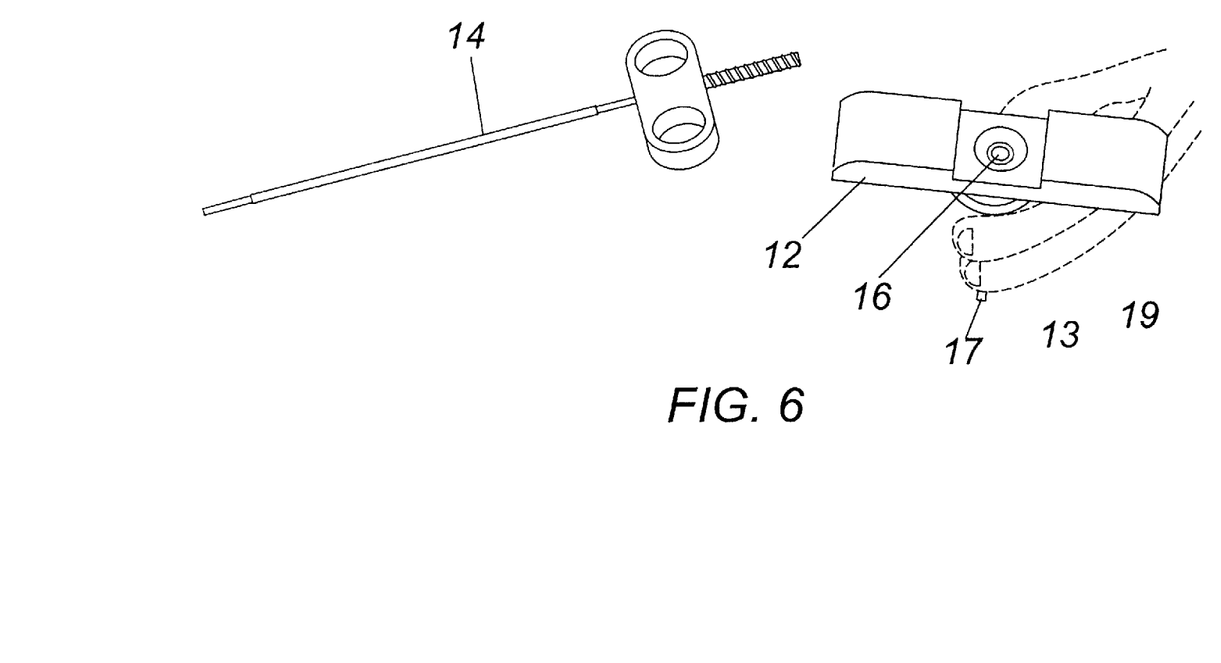
FIG. 6 is a top view of a handle into which a needle is inserted.

FIG. 6 illustrates the hollow cannula 16 into which the needle 22 is slidably located. Also visible in FIG. 6 is funnel 17 which extends from the upper portion 15 of handle 18 to the first end 13 of the inner cannula 16. The funnel 17 includes an open mouth 19 which tapers substantially to the diameter of the inner bore of the inner cannula. The funnel provides the user with an easily targeted aperture for insertion of the needle 22 or a guidewire also known as a Kirshner wire (not shown) often used in spinal as well as other types of surgeries.

Figure 11:
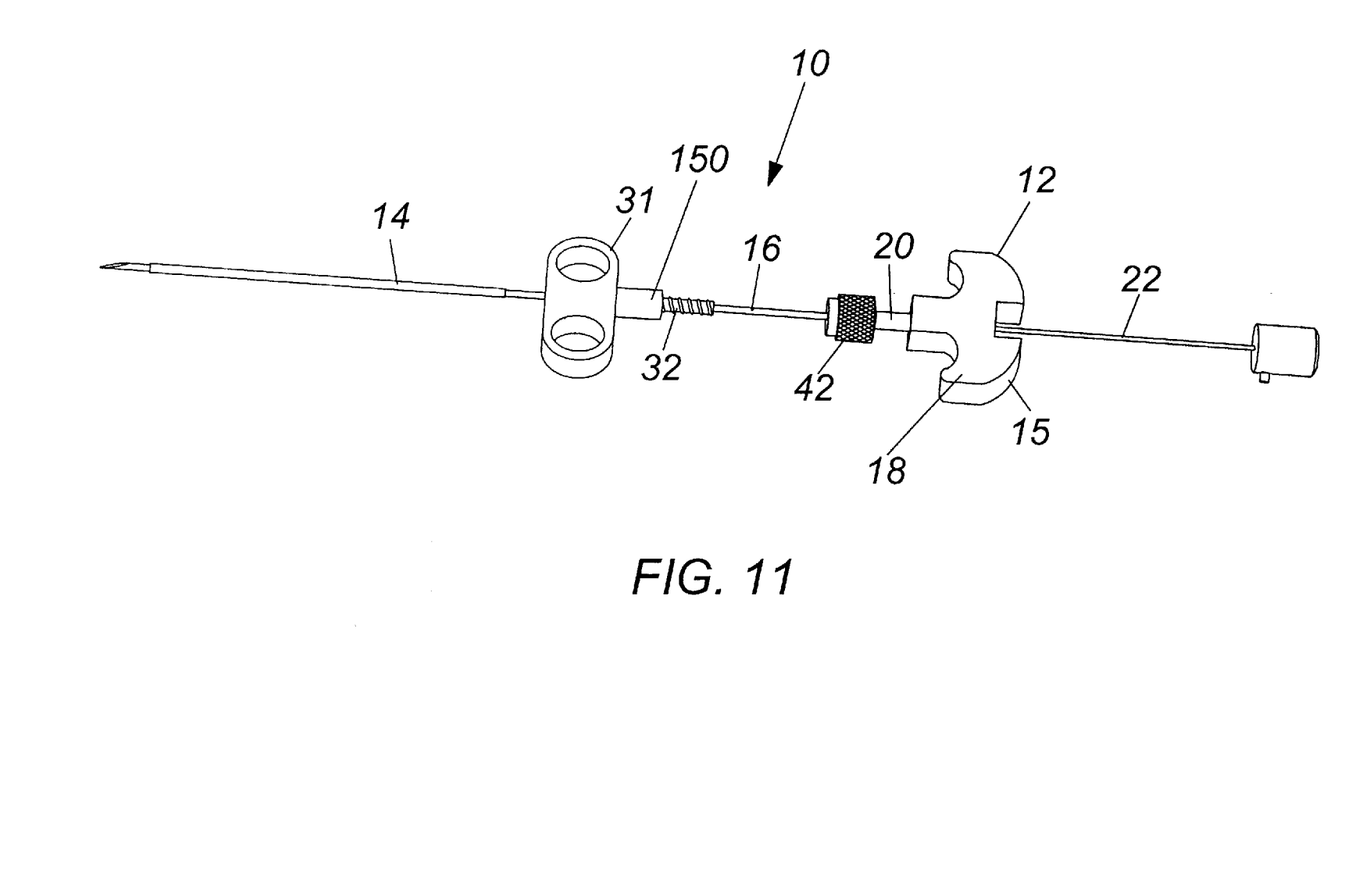
FIG. 11 is a perspective view of the invention of FIG. 1 including an optional stop.

FIGS. 2 and 11 illustrates an optional collar or spacer 150 that can be placed on the sleeve 32. This spacer or collar 150 enables the surgeon or medical technician to precisely place the cannula 16 and needle 22 within a bone or other portion of a patient. The precise desired location of the cannula 16 and needle 22 is first determined by radiography. A measurement of this location is taken, and then a spacer or collar 150 is selected; the length of the spacer corresponding to this measurement. The spacer or collar is then placed over the sleeve 32 and the procedure is performed. In at least one embodiment, the spacer member 150 is U-shaped, an inner portion of the U-shape 151 sized to fit around the threaded member. Therefore, the end of the needle is positioned exactly where the surgeon or medical technician has determined it should be. This optional spacer prevents any over-insertion of the cannula 16 and needle 22.

Figure 8:
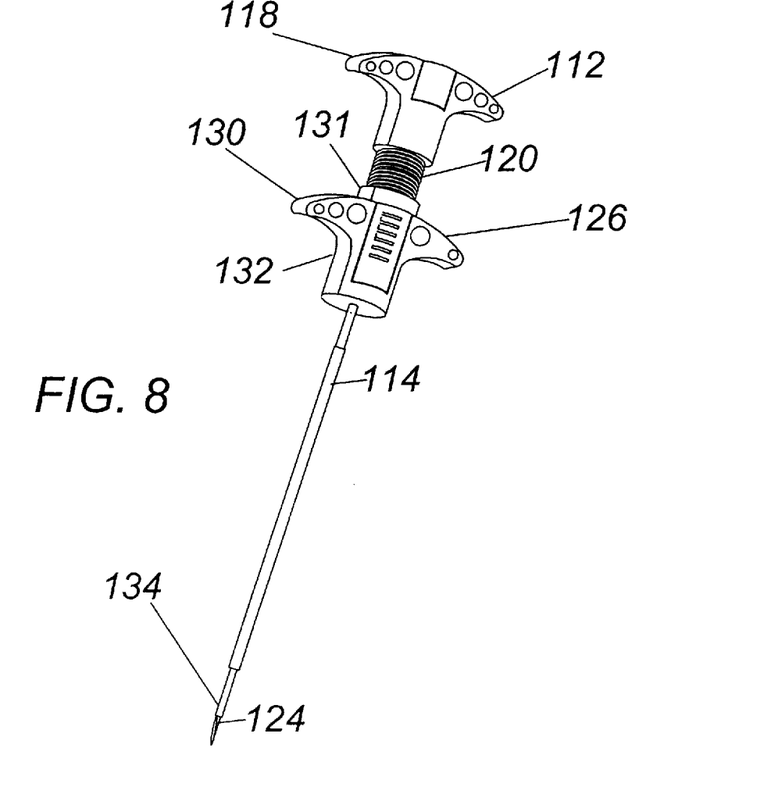
FIG. 8 is a perspective view of an alternate embodiment of the invention in a position similar to FIG. 3.
Figure 9:
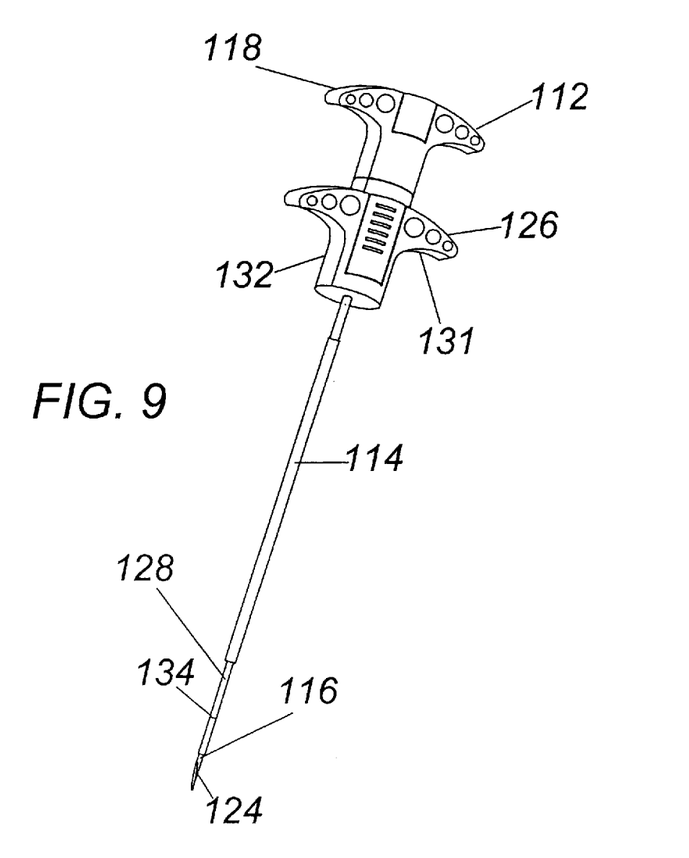
FIG. 9 is a perspective view of an alternate embodiment of the invention in a position similar to FIG. 4.

FIGS. 8 and 9 illustrate an alternate embodiment of the present invention. In these figures a Jamshidi-type assembly 112 is slidably disposed within an outer cannula assembly 114. The Jamshidi-type needle 112 includes a cannula 116 which is secured to a handle 118. The handle 118 includes a threaded collar portion 120. This threaded collar portion 120 is fixedly secured or molded to the handle 118. The handle 118 preferably has an ergonomic shape that can comfortably fit into a surgeon's or medical technician's hand. The handle includes an upper curved portion which is shaped to conform to an individual's palm. The lower portion of the handle 118 is also curved. The curve of the lower portion of the handle is designed to be grasped by the fingers of an individual to assist in the control of the Jamshidi-type assembly 112. The handle 118 is used to drive the cannula into, and sometimes through bones of a vertebra. Sometimes the Jamshidi-type assembly 112 can be driven through the bone only by using pressure exerted by an individual's hand. Other times a hammer or other instrument must be employed to drive the Jamshidi-type assembly 112 through a bone. There is a risk, that when a hammer or similar instrument is utilized, the Jamshidi-type assembly 112 will pass too far into a vertebra. This can cause damage to nerves located nearby. Sometimes the needle passes completely through the vertebra and injures an adjacent blood vessel or internal organ. To prevent this, the present invention utilizes a second cannula 114 which is adjustably secured to the Jamshidi-type assembly 112.

A needle, not shown, is slidably positioned within the cannula 116. This embodiment of the present invention illustrates the needle as having a conical tip 124, however, other tips and needles can also be employed. For example, a trocar needle can be utilized. The tip 124 can be tapered, hollow, etc. The tip can be utilized to extract a tissue sample. It can also be utilized to anchor the needle to a bone. An orthopedic bone screw or other device can then be passed down the needle and secured to the correct location on a bone. While the preferred embodiment of the present invention discloses a relatively rigid needle, other needles which are flexible can also be employed.

The outer cannula 114 comprises an upper portion 126 secured to a cannula 128 (FIG. 8). The upper portion 126 comprises a handle or grip 130. In this embodiment, the outer or second cannula 114 and the handle 130 are fixedly secured to each other. In other embodiments, these elements can be pivotably secured to each other. The lower end 134 of the outer cannula 114 is constructed and arranged to penetrate and pass through bone. While the end 134 is normally a hollow tube with an end that tapers to a sharp edge, other edges can also be employed. For example, the edge can be serrated, saw toothed or sinusoidal. The smooth edge is preferably utilized when the needle assembly is driven straight into or through a bone. The serrations or waves are employed when additional effort is required to penetrate a bone. The handle or grip 130 can be provided with apertures 131 into which a surgeon's fingers can be inserted to control the device.

The Jamshidi-type assembly 112 of this embodiment includes a threaded collar portion 120. The second cannula 114 includes a housing 132 at a top end thereof. The housing is relatively hollow and includes threads which match the threads on sleeve portion 120. After the surgeon inserts the needle into a patient and through the cortical bone 36 of a vertebra, the cannula 116 is inserted further into the vertebra by rotating the handle 118 and sleeve portion 120. Rotation of sleeve 120 moves the cannula 116 and needle further into the vertebra. The distance that these elements are moved can be measured along the sleeve portion. The distance the needle needs to travel into the vertebra, which has been determined by radiography, will be measured along sleeve portion 120. Preferably a mark or indicia is then placed on sleeve portion 120.

The surgeon or medical technician can now rotate handle 118 and sleeve 120 until it reaches the desired mark of indicia on sleeve 120. At this point, the cannula 116 and Jamshidi-type assembly 112 are now exactly where they need to be positioned.

Figure 10:
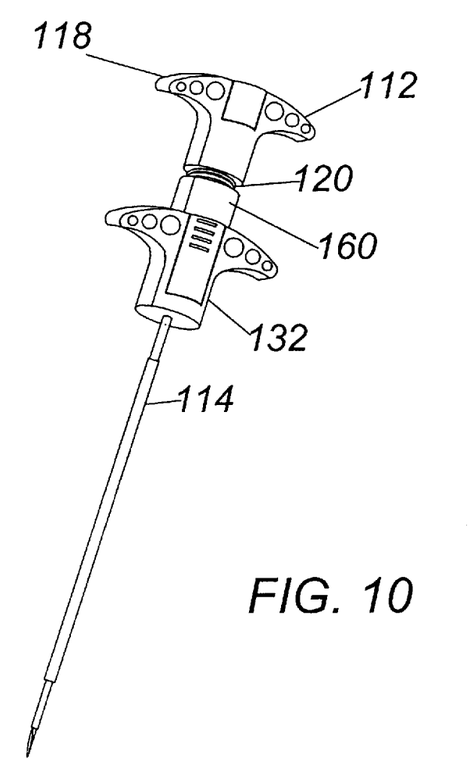
FIG. 10 is a perspective view of an alternative embodiment of the invention including an optional stop.

FIG. 10 illustrates an optional collar or spacer 160 that can be placed on the sleeve 120. This spacer or collar 160 enables the surgeon or medical technician to precisely place the cannula 116 and Jamshidi-type assembly 112 within a bone or other portion of a patient. The precise desired location of the cannula 116 and Jamshidi-type assembly 112 is first determined by radiography. A measurement is taken and then a spacer or collar 160 is selected which corresponds to this measurement. The spacer or collar is then placed over the sleeve 120 and the procedure is performed. This optional spacer prevents any over-insertion of the cannula 116 and Jamshidi-type assembly 112.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A depth controlled jamshidi needle comprising:
an outer cannula assembly, said outer cannula assembly including a substantially rigid first tubular member having a first end and a second end, said first end including a threaded tubular portion positioned around and secured to said first tubular member,
an inner cannula assembly, said inner cannula assembly including a substantially rigid second tubular member having a first end and a second end,
a handle secured to said first end of said inner cannula assembly, a lower portion of said handle including a threaded member constructed and arranged to cooperate with said threaded tubular portion of said outer cannula assembly, said lower portion of said handle including a bearing, said threaded member secured to said bearing for rotation whereby rotation of said threaded member, without rotation of said handle, causes linear movement of said inner cannula assembly within said outer cannula assembly, an upper portion of said handle including a first portion of a fastener constructed and arranged for removable attachment to a needle member,
a needle member including a first end and a second end, said first end including the second portion of said fastener for removably securing said needle member to said handle, whereby rotation of said handle causes linear movement of said inner cannula assembly within said outer cannula assembly.

2. The jamshidi needle of claim 1 including a grip member secured to said first end of said outer cannula assembly, said grip member constructed and arranged for application of a counter rotating force with respect to a rotating force applied to said handle member.

3. The jamshidi needle of claim 1 wherein said first and said second portions of said fastener include helical threads for engagement therebetween.

4. The jamshidi needle of claim 3 wherein said helical threads include indicia to indicate the distance of said linear movement.

5. The jamshidi needle of claim 1 wherein said first and said second portions of said fastener include a bayonet type configuration for engagement therebetween.

6. The jamshidi needle of claim 1 wherein said second end of said second tubular member tapers to a substantially sharp edge.

7. The jamshidi needle of claim 1 wherein said handle is removably secured to said first end of said inner cannula assembly.

8. The Jamshidi needle of claim 1 wherein said needle member is solid.

9. The jamshidi needle of claim 1 including a spacer member having a predetermined length, said spacer member constructed and arranged to cooperate with said threaded tubular portion to provide a stop to control said linear movement of said inner cannula assembly within said outer cannula assembly.

10. The jamshidi needle of claim 9 wherein said spacer member is U-shaped, an inner portion of said U-shape sized to fit around said threaded member.

11. The jamshidi needle of claim 1 wherein said upper portion of said handle includes a funnel, said funnel constructed and arranged to provide guidance to the inner aperture of said inner cannula assembly.

12. A depth controlled jamshidi needle comprising:
an outer cannula assembly, said outer cannula assembly including a substantially rigid first tubular member having a first end and a second end, said first end including a first portion of a linear translation assembly positioned around and secured to said first tubular member,
an inner cannula assembly, said inner cannula assembly including a substantially rigid second tubular member having a first end and a second end, said first end of said inner cannula assembly including a second portion of a linear translation assembly,
a handle secured to said first end of said inner cannula assembly, a lower portion of said handle constructed and arranged to cooperate with said first end of said second tubular member, said lower portion of said handle includes a bearing, said threaded member secured to said bearing for rotation whereby rotation of said threaded member, without rotation of said handle, causes linear movement of said inner cannula assembly within said outer cannula assembly, an upper portion of said handle including a first portion of a fastener constructed and arranged for removable attachment to a needle member,
a needle member including a first end and a second end, said first end including the second portion of said fastener for removably securing said needle member to said handle,
whereby operation of said linear translation assembly causes linear movement of said inner cannula assembly within said outer cannula assembly.

13. The jamshidi needle of claim 12 wherein said first end first portion of said linear translation assembly includes a threaded tubular portion positioned around and secured to said first tubular member, and said first end of said second tubular member includes a second threaded member constructed and arranged to cooperate with said threaded tubular portion of said outer cannula assembly.

14. The jamshidi needle of claim 12 wherein said second threaded member is secured to said lower portion of said handle.

15. The jamshidi needle of claim 12 wherein said upper portion of said handle includes a funnel, said funnel constructed and arranged to provide guidance to the inner aperture of said inner cannula assembly.

* * * * *